United States Patent [19]

Roach et al.

[11] 4,048,556
[45] Sept. 13, 1977

[54] METHOD FOR EVALUATING ELECTRODE CONSUMPTION RATE

[75] Inventors: Maurice P. Roach; Stanley L. Strudthoff, both of Cedar Falls, Iowa

[73] Assignee: Deere & Company, Moline, Ill.

[21] Appl. No.: 672,307

[22] Filed: Mar. 31, 1976

[51] Int. Cl.² .............................................. G01R 33/14
[52] U.S. Cl. ........................................ 324/40; 13/13
[58] Field of Search .......................... 324/40; 13/1, 13

[56] References Cited
U.S. PATENT DOCUMENTS 3,170,082  2/1965  Renborg ................................. 13/13

*Primary Examiner*—M. Tokar

[57] ABSTRACT

A method for determining the expected consumption rate of graphite electrodes is disclosed. An electrical signal is applied to a number of electrodes to generate eddy currents therein which are sensed to provide eddy current values. The consumption rate of the electrodes in use in an electric arc metallurgical furnace are measured. A standard eddy current value (with respect to the measured consumption rates) is determined, for example, by plotting the eddy current values and measured consumption rates. Thereafter, eddy current values obtained from other electrodes are compared with the standard eddy current value to determine the expected consumption rate.

10 Claims, 4 Drawing Figures

METHOD FOR EVALUATING ELECTRODE CONSUMPTION RATE

BACKGROUND OF THE INVENTION

The use of electric arc furnaces in metallurgy, both ferrous and non-ferrous, has been increasing at a substantial rate. In the electric arc furnace process, graphite electrodes are consumed. Electrode consumption rates vary greatly from electrode to electrode and can vary, for example, from 3 to 25 pounds per ton of metal (e.g., steel, iron, copper). Thus, the consumption of graphite electrodes has also been increasing at a substantial rate. The cost of the graphite electrode generally is from about 7 to 12 percent of the total raw material cost charged into the electric furnace and is thus a significant cost variable in this type of process.

One of the disadvantageous features of graphite electrodes for use in electric arc metallurgical furnaces is the inability to predict the consumption rate of a given electrode. That is, while a group of electrodes may be produced in the same manner and may visually be essentially identical, the consumption rate of one electrode may be twice that of another electrode within the same group.

It would be desirable to have a standard, minimum consumption rate (for example, a minimum consumption rate for a particular type and size of electrode). However, there is presently no method of determining how long an electrode will last in use other than the actual consumption rate itself. The need exists for a method of determining, before a particular electrode is used, the approximate consumption rate.

In recent years, attempts have been made to correlate various physical properties of the electrodes used in the electric arc metallurgical furnaces with consumption rate. The properties generally considered have included density, mechanical strength, modulus of elasticity, thermal conductivity, electrical resistivity, oxidation rate and apparent porosity. In these investigations, samples are generally taken from the socket end of the electrode and the various properties measured. However, the results obtained have not satisfactorily equated any or all of these properties with the consumption rate. In addition, the proposed method is destructive of the electrode itself (or at least a part of the electrode) and requires a relatively skilled technician and/or extensive laboratory equipment.

OBJECTS AND SUMMARY OF THE INVENTION

It is an object of this invention to provide a method for predicting the consumption rate of graphite electrode to be used in an electric arc furnace which avoids or alleviates the problems of the prior art.

It is also an object of the present invention to provide a rapid, relatively simple determination for the predicted consumption rate of a graphite electrode to be used in an electric arc furnace, which determination may be performed by a relatively unskilled operator in electric arc furnace production facilities.

Another object of the present invention is to provide a non-destructive test for a graphite electrode to be used in an electric arc furnace which allows the establishing of a minimum rate of consumption for the electrode.

Other objects and advantages of the present invention will become apparemt from the following:

In accordance with the present invention, there is provided a method of graphite electrodes which comprises applying an electrical signal to a number of the plurality of graphite electrodes to generate eddy currents in said electrodes. These generated eddy current are sensed to obtain eddy current values. The consumption rate of these number of electrodes is measured and a standard eddy current value is determined with respect to the measured consumption. The eddy current values obtained from the remaining plurality of graphite electrodes is compared with the standard eddy current value to determine the approximate consumption rate of these remaining electrodes.

These and other objects and advantages of the present invention will be readily apparent to one skilled in the art to which the invention pertains from the claims and following more detailed description of a preferred embodiment when read in conjunction with the appended drawing.

DESCRIPTION OF THE PREFERRED EMBODIMENT

Figure 1:
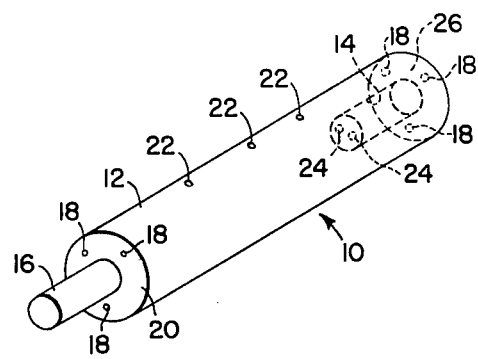
FIG. 1 is a pictorial view of a typical solid graphite electrode used in an electric arc furnace.

Referring to FIG. 1, a solid graphite electrode for use in an electric arc furnace is generally designated as 10. The electrode 10 generally has a main body section 12 having a socket 14 at one end and a nipple section 16 at the other end. Generally, the socket 14 and nipple section 16 are provided with female and male screw threads which are not shown in FIG. 1. As understood by the skilled artisan, graphite electrodes such as shown in FIG. 1 are used in tandem fashion in which the nipple section 16 of one electrode is screwed into a socket 14 of another electrode where they frictionally engage and wedge the two electrodes together.

In accordance with the present invention, electrical signals are applied to the solid graphite electrode 10 to generate eddy currents in the electrode.

Eddy current generation is well-known in the art. Basically, eddy currents are induced in the specimen being tested by an electromagnetic coil in the shape of a probe. Part of the electromagnetic energy of the coil is absorbed and converted into heat while at least part of the remaining energy is reflected back to the coil. Since the electrical characteristics of the reflected energy are changed in a manner determined by the properties of the specimen being tested, they are a source of information describing certain characteristics of the specimen.

Any conventional eddy current tester may be utilized in the practice of the present invention. Portable, light weight units are preferred because of the ease of utilizing these units in production facilities. Conventional portable eddy current testers having a contact probe and without set-up and balance controls (thereby providing an instrument which is operational as it is turned on) have proved advantageous. Such instruments are commercially available and well-known to those skilled in the art. Eddy current testing instruments have numerical scales which provide a numerical value for the eddy current values.

Although the contact probe of the eddy current tester which applies the electrical signal which generates the eddy current may be applied at any convenient point on the electrode 10, it has been found advantageous to apply the contact probe at each of three equispaced points 18 located on the flat end face 20 of the main body section 12 from which the nipple section 16 extends and on flat end face 26 on the socket end of the main body section 12. The contact probe may also be applied at three spaced points 22 along the length of the electrode 10 and/or at points 24 near the center of the socket end of the electrode. Application of the contact probe of the eddy current tester at points 18 (or 22 or 24) yields readings on the eddy current tester scale of eddy current values. Since many eddy current testers have different scales based on differing frequency standads (Hertz), a scale should be chosen which produces an accurate reading.

In operation, one or a number of graphite electrodes are contacted with an eddy current tester to obtain an eddy current value or values. If readings are obtained at more than one point (that is, at the six points 18 or three points 22 or two points 24), these readings may be averaged to provide a single value per electrode per position on the electrode.

The electrode or electrodes which have thus been measured are then utilized in conventional fashion in an electric arc metallurgical furnace. The consumption rate of the electrode (in terms of pounds of electrode consumed per ton of metal) melted is determined for each electrode by measuring the weight of each electrode and the tons of metal melted per heat for each electrode.

Figure 2:
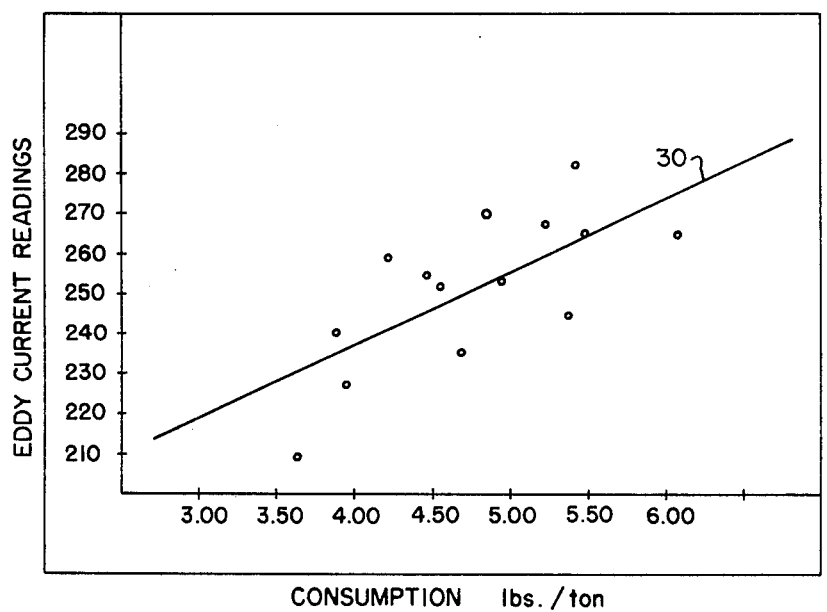
FIG. 2 is a graphical representation of eddy current values obtained from particular points on graphite electrode samples plotted versus consumption rate of the electrodes when used in an electric arc furnace.

The measured consumption rate is compared with the measured eddy current values, generally by graphically plotting the measurements. FIG. 2 is a graph of eddy current readings obtained at points 18 of particular electrodes (using the average of the six readings obtained for each electrode as one eddy current reading) versus the consumption rate in pounds of the electrode per ton of metal melted in the use of such electrode. The plot of these points (by linear regression analysis) yields a straight line corresponding to the equation.

$$\text{Eddy Current Reading} = k_1 (\text{Consumption Rate}) + k_2 \quad (1)$$

In this instance, $k_1$ is 19.05 and $k_2$ is 161.03. The correlation coefficient between Equation (1) and the data obtained is over 70%.

Figure 3:
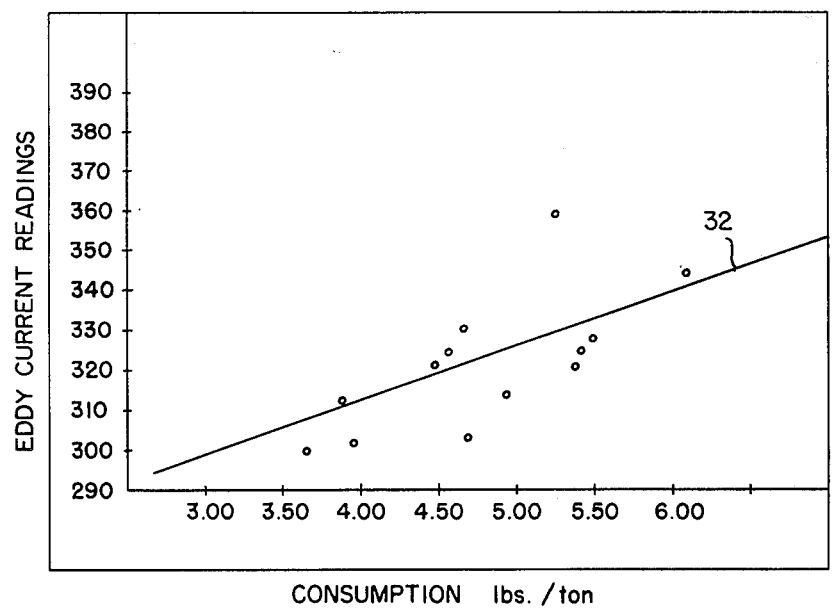
FIG. 3 is a graphical representation of eddy current values obtained from particular points of graphite electrode samples plotted versus consumption rate of the electrodes when used in an electric arc furnace.
Figure 4:
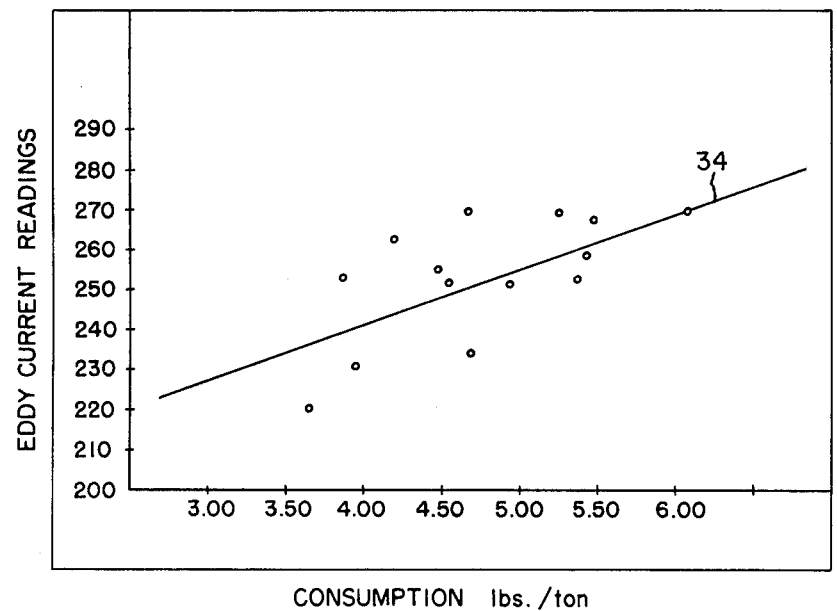
FIG. 4 is a graphical representation of eddy current values obtained from particular points on graphite electrode samples plotted versus consumption rate of the electrodes when used in an electric arc furnace.

FIGS. 3 and 4 are similar plots in which the eddy current values are obtained by measurements along the length of the electrode (points 22) and at the center of the ends of the electroe (points 24), respectively. Again, the points obtained may be expressed as a straight-line function although the $k_1$ and $k_2$ values for each function vary.

The straight lines 30, 32 and 34 (FIGS. 2, 3 and 4, respectively) represent a standard correlation of the consumption rate of a particular electrode as a function of the eddy current values obtained at a particular point on the electrode prior to use. Thus, the establishment of a graph such as shown in FIGS. 2, 3 or 4 provides a reasonable prediction of consumption rate for another electrode before it is utilized. For example, if an electrode yields an average eddy current reading at points 18 of 250, the consumption rate of that electrode should be approximately 4.70 pounds of electrode per ton of metal. It has been found that the predicted consumption values are within about ± 12% or less of the actual consumption values obtained with the measured electrode. In this manner, electric arc furnace production facilities can predict, within reasonable limits, the time when electrode additions will be necessary in a particular production run and the amount of electrodes which will be necessary to process a given amount of metal.

The present invention may also be utilized as a quality control on electrodes. That is, if it is desired that any electrodes utilized in an electric arc furnace be capable of providing a standard consumption rate of, for example, 4.50 pounds of electrode per ton of metal or less, then the eddy current values obtained from that electrode by correlation with the appropriate standard correlation may be used to predict the estimated consumption rate. For example, utilizing FIG. 2, an electrode yielding an average eddy current value of 270 has an estimated consumption rate of about 5.77 pounds of electrode per ton of metal, a value far in excess of the standard consumption rate. Such an electrode may not be efficiently utilizable in an electric arc furnace. In this manner, users of electrodes in electric arc furnaces may be able to generate standard consumption rate figures for electrode manufacturers to ensure that the electrodes received may be efficiently utilized in the electric arc furnace process.

The process of the present invention thus provides a rapid, relatively simple determination for the estimated consumption rate of graphite electrodes for use in the electric arc furnace process. Although the above description and FIG. 1 refer to solid graphite electrodes, it will be understood that the present invention is also applicable to hollow graphite electrodes as conventionally utilized in electric arc metallurgical furnaces. Eddy current testers are commercially available, lightweight and relatively simple to operate. Although the preparation of the correlation between the eddy current values and the consumption rate can be obtained by measuring and plotting the appropriate data for any number of electrodes, it will be understood by those skilled in the art that the larger the number of these initial points, the more accurate the resulting correlation will be. The particular numbe may vary considerably but a statistically significant number of electrodes should be measured. Once the correlation data has been obtained, the resulting correlation has been found to be useful in the determination of the consumption rate of graphite electrodes of the same size, shape, grade, and manufacturer. The correlatable relationship of eddy current values to consumption rate appears to be maintained. Although the specific constants in the linear equation may vary, from manufacturer to manufacturer, from one particular electrode phase of an electric arc furnace to another, in the grade of graphite and from arc furnace to arc furnace.

The invention is additionally illustrated in connection with the following Example which is to be considered as illustrative of the present invention. It should be understood, however, that the invention is not limited to the specific details of the Example.

EXAMPLE

Eddy current tests are performed on a series of solid graphite electrodes to be used in electric arc furnace iron making. Each electrode is shaped like the electrode of FIG. 1 and is 72 inches in total length with a 14 inch outside diameter of the main body section. The nipple section is 10.66 inches in length and 6.975 inches in diameter. The electrodes each weigh about 610 pounds.

Eddy current values for each electrode are obtained from points 18 (FIG. 1) on the flat end of the main body section, points 22 along the length of the electrode and points 24 on the center of the ends of the electrode. The eddy current tester utilized is a commercially available portable eddy current tester ("Verimet 1900," K. J. Law Engineers, Inc.) with a frequency of 100 kilohertz.

Each electrode is thereafter utilized in a conventional manner in the same electrode column in an electric arc furnace. The consumption rate for each electrode is determined by calculating the total amount of tons of iron produced per electrode when the electrode butt end is one foot from the adjacent electrode section.

The eddy current and consumption rate values obtained are shown below in Table I and are also shown graphically in FIGS. 2, 3 and 4. The eddy current values shown are the average for each location of all the values obtained per electrode.

TABLE I

| | Eddy Current Values | | | |
|---|---|---|---|---|
| Electrode | Flat End of Body Section | Length of Electrode | Center of Ends | Consumption Rate lbs electrode/ton iron |
| A | 255 | 321 | 255 | 4.47 |
| B | 244 | 321 | 253 | 5.37 |
| C | 227 | 302 | 231 | 3.94 |
| D | 259 | — | 261 | 4.22 |
| E | 282 | 325 | 259 | 5.42 |
| F | 267 | 359 | 269 | 5.24 |
| G | 210 | 300 | 221 | 3.65 |
| H | 235 | 303 | 234 | 4.68 |
| I | 252 | 324 | 252 | 4.55 |
| J | 269 | 330 | 270 | 4.66 |
| K | 265 | 328 | 268 | 5.48 |
| L | 254 | 314 | 251 | 4.93 |
| M | 266 | 344 | 270 | 6.06 |
| N | 241 | 312 | 253 | 3.88 |

After the above data is plotted, the straight line standard correlation shown in the Figures is obtained.

Further electrodes are tested to obtain eddy current values in the manner noted and estimated consumtion rates are obtained from FIGS. 2, 3 and 4. The actual consumption rates are measured in the same manner as described above. Table II shows the data obtained.

TABLE II

| | Eddy Current Values | | | Consumption Rate lbs electrode/ton steel | |
|---|---|---|---|---|---|
| Electrode | Flat End of Body Section | Length of Electrode | Center of Ends | Estimated | Actual |
| $O_1$ | — | — | 245 | 4.30 | 3.95 |
| $P_1$ | — | — | 265 | 5.75 | 5.40 |
| $Q_1$ | — | — | 225 | 2.80 | 3.00 |
| $O_2$ | 240 | — | — | 4.20 | 3.95 |
| $P_2$ | 260 | — | — | 5.23 | 5.40 |
| $Q_2$ | 220 | — | — | 3.05 | 3.00 |
| $R_1$ | 235 | — | — | 3.90 | 3.75 |
| $S_1$ | 250 | — | — | 4.75 | 4.60 |
| $T_1$ | 280 | — | — | 6.30 | 6.10 |
| $R_2$ | — | 305 | — | 3.60 | 3.75 |
| $S_2$ | — | 325 | — | 4.90 | 4.60 |
| $T_2$ | — | 345 | — | 6.35 | 6.10 |

As may be seen from Table II, the estimated consumption rate for the electrodes tested correlated well with their actual consumption rate. The correlation was somewhat better with the eddy current values obtained from that flat end of the body section (points 18). In all cases, however, the present invention provided a reasonably accurate, non-destructive method for predicting the consumption rate of the electrodes in an electric arc furnace.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A method of determining the approximate consumption rate of a plurality of graphite electrodes which comprises:
    applying an electrical signal to a number of the plurality of graphite electrodes to generate eddy currents in said electrodes;
    sensing the generated eddy current to obtain eddy current values;
    using said number of electrodes in an electric arc furnace and measuring the consumption rate of each of the said number of electrodes during said use;
    determining a standard correlation between eddy current values and the said measured consumption rates; and
    comparing the eddy currents values obtained from the remaining plurality of graphite electrodes with the standard eddy current correlation value to determine the approximate consumption rate thereof.

2. The method of claim 1 wherein the said electrical signals are applied to a flat section of the electrode.

3. The method of claim 1 wherein the said electrical signals are applied along the length of the electrode.

4. The method of claim 1 wherein the said standard eddy current value is obtained by plotting the eddy current values and consumption rates of said number of electrodes.

5. A method of testing a graphie electrode for expected consumption rate in an electric arc furnace which comprises:
    applying an electrical signal to a portion of the said graphite electrode to generate eddy currents therein;
    sensing the generated eddy currents to obtain an eddy current value;
    comparing the obtained eddy current value with a standard representing the correlation between eddy current values and consumption rate to determine the expected consumption rate thereof.

6. The method of claim 5 wherein the standard eddy current value is obtained by establishing measured eddy current values and measured consumption rates for a number of graphite electrodes.

7. The method of claim 6 wherein all of the measured eddy current values are obtained at the same portion of the electrode.

8. The method of claim 7 wherein the portion of the electrode is a flat section on the electrode body.

9. The method of claim 7 wherein the portion of the electrode is along the length of the electrode body.

10. The method of claim 5 wherein the graphite electrode is a solid graphite electrode.

* * * * *